United States Patent
Witham et al.

(10) Patent No.: US 7,951,387 B2
(45) Date of Patent: May 31, 2011

(54) EYELID SCRUB COMPOSITION

(75) Inventors: Patrick Witham, Eugene, OR (US); Nat G. Adkins, Jr., Richmond, TX (US); Daniel Banov, Sugar Land, TX (US); August Bassani, Houston, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 928 days.

(21) Appl. No.: 11/592,684

(22) Filed: Nov. 3, 2006

(65) Prior Publication Data

US 2008/0131470 A1   Jun. 5, 2008

(51) Int. Cl.
*A61K 8/43* (2006.01)
*A61K 47/00* (2006.01)
*A61M 35/00* (2006.01)

(52) U.S. Cl. ......... 424/401; 514/249; 514/784; 514/788

(58) Field of Classification Search .................. 424/401, 424/423, 487; 514/165, 249, 564; 510/112, 510/119, 130, 421, 470, 476, 488
See application file for complete search history.

(56) References Cited

U.S. PATENT DOCUMENTS

| | | | |
|---|---|---|---|
| 4,654,208 A | 3/1987 | Stockel et al. | |
| 4,758,595 A | 7/1988 | Ogunbiyi et al. | |
| 5,470,875 A | 11/1995 | Merianos et al. | |
| 5,702,992 A | 12/1997 | Martin et al. | |
| 5,942,218 A | 8/1999 | Kirschner et al. | |
| 6,045,817 A | 4/2000 | Ananthapadmanabhan et al. | |
| 6,207,628 B1 * | 3/2001 | Soyer et al. | 510/112 |
| 6,642,198 B2 * | 11/2003 | Pflederer et al. | 510/434 |
| 6,846,846 B2 | 1/2005 | Modak et al. | |
| 2001/0036964 A1 * | 11/2001 | Clarkson et al. | 514/564 |
| 2002/0128170 A1 | 9/2002 | DeClercq et al. | |
| 2004/0259951 A1 | 12/2004 | Clarkson et al. | |
| 2005/0048139 A1 | 3/2005 | Modak et al. | |
| 2005/0238602 A1 | 10/2005 | Modak et al. | |
| 2005/0261401 A1 | 11/2005 | Wood et al. | |
| 2005/0269401 A1 | 11/2005 | Wood et al. | |
| 2005/0281762 A1 | 12/2005 | Modak et al. | |
| 2006/0045858 A1 * | 3/2006 | Fuller | 424/59 |
| 2006/0093634 A1 * | 5/2006 | Lutz et al. | 424/401 |
| 2006/0246013 A1 | 11/2006 | Adkins, Jr. | |
| 2007/0110792 A9 * | 5/2007 | Simon | 424/443 |
| 2009/0312337 A1 * | 12/2009 | Graham et al. | 514/249 |

FOREIGN PATENT DOCUMENTS

| | | |
|---|---|---|
| GB | 1167249 | 10/1969 |
| WO | WO 03/069994 | 8/2003 |
| WO | WO 2005/097130 | 10/2005 |
| WO | WO 2006/045743 | 5/2006 |
| WO | WO 2007/120817 | 10/2007 |

OTHER PUBLICATIONS

Aging Eye Times, [Online], May 5, 2003, pp. 1-4, retrieved from www.agingeye.net/otheragingeye/blepharitis.php (retrieved on Apr. 2, 2008).
Hansmann F. et al. Polyhexamethylenbiguianid (PHMB) aur praoperativen Antisepsis bei Kataraktoperation: Der Opthalmologe, vol. 4, 2004, pp. 377-383, XP00247453.
Key J.M.: A Comparative Study of Eyelid Cleaning Regimens in Chronic Blepharitis: The CLAO Journal, vol. 22, No. 3, Jun. 1996 pp. 209-212, XP009093078.
Greiner J.V. et al. "Effects of Eyelids Scrubbing on the Lid Margin" The CLAO Journal, vol. 25, No. 2, Apr. 1999 pp. 109-113, XP009098075.
Polack F.M. et al,Liebowitz H.M. et al. "Experience with a new detergent lid scrub . . . chronic blepharitis . . . " Arch Opthalmol, vol. 106, Jun. 1988, pp. 719-720, XP009098098.
Written Opinion, IP Australia.
Lomax, Eric G.; "Amphoteric Surfactants:" Surfactant Science Series, vol. 59, Second Edition 1996 Marcel Dekker, Inc; New York, New York; USA http://books.google.com/books?id = f2bJVtfN0t8C&source=gbs_navlinks_s.

* cited by examiner

*Primary Examiner* — Michael G Hartley
*Assistant Examiner* — Jagadishwar R Samala
(74) *Attorney, Agent, or Firm* — D'Ambrosio & Menon, LLP; Usha Menon; Srikant Viswanadham

(57) ABSTRACT

An eyelid scrub composition comprising polyhexamethylene biguanide (PHMB), 1,2-hexanediol, 1,2-octanediol, and a pH stabilizing surfactant solution present in an amount effective to control the pH level of the composition between 5.5 and 7.5. The composition can further comprise moisturizers and foam stabilizers. The composition can be combined with a fabric pad for use as an eyelid scrub, where the fabric pad is pre-moistened with the composition and packaged for use. The composition may be applied to the eyelid scrub and rubbed to induce foaming. The composition is produced by preparing a modified Ringer's solution and adding 1,2-hexanediol, 1,2-octanediol, and an effective amount of one or more pH stabilizing surfactants. The mixture is then heated and allowed to cool before polyhexamethylene biguanide is added.

22 Claims, 1 Drawing Sheet

EYELID SCRUB COMPOSITION

FIELD OF THE INVENTION

The present invention relates to an anti-microbial composition. Further, the invention relates to compositions useful as eyelid scrubs.

BACKGROUND OF THE INVENTION

The eyelids are important to over-all ocular health because they protect the eyes from dangers such as approaching objects or from airborne contaminants, such as pollen, dust particles or other foreign bodies. The eyelids contain several glands including the lacrimal glands and meibomian glands that produce layers of tear film that are critical for healthy eyes. When an individual blinks, a new tear film is created and tears are distributed across the cornea to lubricate the surface of the eye. This blinking action also "flushes" foreign materials from the eye.

The eyelids, however, are subject to certain problems, which while common, are none-the-less bothersome, especially for contact lens wearers, and may lead to other, more serious complications. One complication is staphylococcal blepharitis (blepharitis). Blepharitis is a common chronic inflammation of the eyelids characterized by a scaly crust on the lid margins. The condition may be caused by a bacterial infection, or it may be allergic in origin or associated with seborrhea of the face and scalp. Treatment usually involves cleansing the eyelids on a regular basis to remove excess oil, debris, and desquamated skin that may be problematic.

Often associated with or secondary to blepharitis is a bacterial infection of the surface of the skin at the edge of the lid, known as an internal hordeolum. Other such infections include external hordeolum, commonly referred to as styes, which are infections of the tiny oil secreting meibomian glands along the edge of the eyelid, surrounding the eyelashes. A stye begins as a red, tender bump and usually fully develops within three days. Such conditions are accompanied by pain, redness and tenderness of the lid margins. Although styes are often recurring, regular cleansing of the eyelid margins can minimize such conditions. A second problem is a chalazion, which is an inflammation of the meibomian glands inside the eyelid. Chalazia typically grow slowly over 2-3 weeks and although they do not typically cause pain, they often require surgical intervention if left untreated.

With any of the above-described problems, as well as other medical complications, such as rosacea and seborrhea, proper eyelid hygiene with the use of an eyelid cleanser may minimize the severity of the outbreak, or prevent the problem altogether if caught early. Eyelid cleansers are also used for cleaning eyelashes, eyelids or the periocular area and may be used as a pre-operative scrub to help reduce the presence of harmful bacteria which may cause infection, inflammation, or even endophthalmitis in patients.

Endophthalmitis is an intraocular infection that commonly occurs after cataract surgery. The causative agent in post-operative endopthalmitis is typically a bacteria, often the causative bacteria is *Staphylococcus Epidermidis*. To prevent post-operative endopthalmitis as well as blepharitis, an eyelid scrub is often used to cleanse the eyelid.

Often simple skin cleansers are unsuited for use on the eyelid. Eyelid cleansers must be non-irritating to both the sensitive skin around the eye and the eye tissue itself, while having an antimicrobial effect. One factor causing eye irritation is an abnormal pH level of the eyelid cleaner composition. Non-irritating formulations should have a pH level which is close to neutral, 7.0. Many skin cleaners have a pH outside this range. To control the pH level of skin cleanser a traditional pH adjuster is often employed. Traditional pH adjusters include basic pH adjusters, such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine), and acidic pH adjusters, such as mineral acids and polycarboxylic acids (e.g., hydrochloric acid, nitric acid, phosphoric acid, sulfuric acid, citric acid, glycolic acid, and lactic acid). Unfortunately, pH adjusters can also cause eye irritation themselves. Therefore, there is a need for an eyelid scrub composition which is effective at killing bacteria, but does not include traditional pH adjusters, so that it is gentle enough to be used around the eye.

SUMMARY

The composition of the present invention is effective as an anti-microbial, while being minimally irritating to the eye. The composition comprises polyhexamethylene biguanide (PHMB), 1,2-hexanediol, 1,2-octanediol, and a pH stabilizing surfactant solution present in an amount effective to control the pH level of the composition between 5.5 and 7.5. The use of a surfactant solution to control pH rather than traditional pH adjusters, makes the composition less irritating to the eye. Also, the foaming capability of the surfactant solution included in the composition increases its cleansing ability.

In one embodiment, the pH stabilizing surfactant solution comprises cocoamphodiacetate disodium, polyoxyethylene 80 sorbitan monolaurate, decyl polyglucoside, and a modified Ringer's solution.

In another embodiment, the composition also includes moisturizers, such as methyl gluceth-20, sorbital, glycerine, glycols, propylene glycol, carboxylates, amino acids, glucoside derivatives, urea, lactates, and derivatives of pantothenic acid.

The composition is produced by preparing a modified Ringer's solution by mixing electrolytes in water and mixing 1,2-hexanediol, 1,2-octanediol, and an effective amount of one or more pH stabilizing surfactants with the modified Ringer's solution. The mixture is then heated and allowed to cool before polyhexamethylene biguanide is added.

The composition may be applied to the eyelid by applying an effective amount of the composition to the eyelid. Optionally, the composition may be rubbed onto the eyelid to induce foaming.

The composition can be combined with a fabric pad for use as an eyelid scrub. The fabric pad is pre-moistened with the composition and packaged for use.

DETAILED DESCRIPTION

Figure 1:
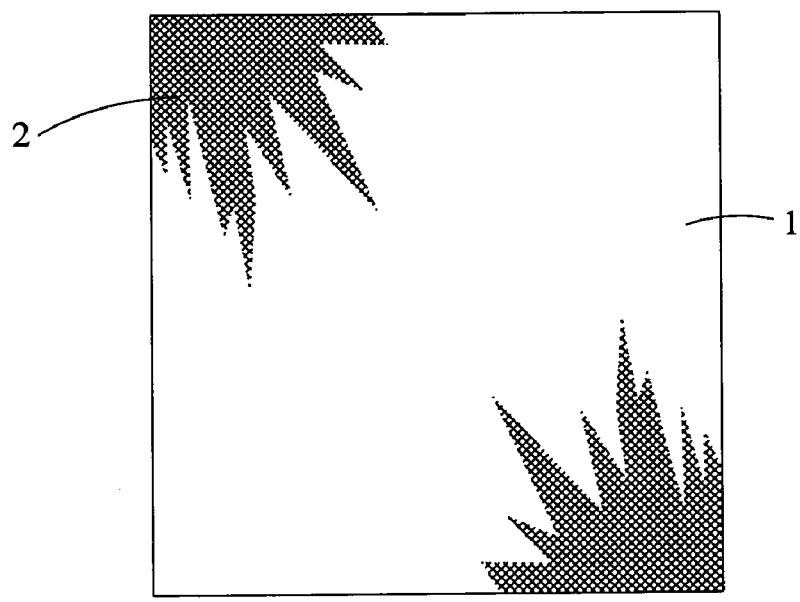
FIG. 1 is a top view of the fabric pad of the invention.

The composition of the invention is effective as an eyelid cleanser, or scrub, as it has an antimicrobial effect, but is still practically non-irritating to the eye. The composition has these beneficial characteristics because of the combination of polyhexamethylene biguanide (PHMB) and Symdiol. Symdiol is a combination of 1,2-hexanediol and 1,2-octanediol. The PHMB-Symdiol combination has a synergistic anti-microbial effect. In addition, the composition of this invention avoids traditional pH adjusters by using a pH stabilizing surfactant solution. Elimination of traditional pH adjusters reduces the amount of irritation caused by the composition in comparison to prior eyelid cleansers.

The eyelid scrub composition of this invention comprises polyhexamethylene biguanide (PHMB), 1,2-hexanediol, 1,2-octanediol, and a pH stabilizing surfactant solution present in an amount effective to control the pH level of the composition between 5.5 and 7.5.

For the purposes of this invention, polyhexamethylene biguanide (PHMB) is pseudonymous for polyhexamethylene biguanide, polyhexamethylene biguanide hydrochloride, and polyaminopropyl biguanide. PHMB is available in a 20% aqueous solution sold under the tradename Cosmocil® by Arch Personal Care Products L.P. The combination of 1,2-hexanediol and 1,2-octanediol is sold under the tradename Symdiol 68 by Symrise. 1,2-octanediol is also known as caprylyl glycol. Combining PHMB with 1,2-hexanediol and 1,2-octanediol has a synergistic antimicrobial effect.

To avoid the irritating effects of traditional pH adjusters, the pH stabilizing surfactant solution is prepared to provide a pH stabilized composition. Surfactants also increase cleansing ability of the composition and have a foaming capability. PHMB is most effective as an antimicrobial agent in pH ranges between 5.5 and 7.5. Therefore, it is desirable to control the pH level of the composition within this range by use of a blend of surfactants. It is also desirable that the eyelid scrub of the present invention has a foaming ability to facilitate physical cleansing of the eyelid. Consequently, surfactants must be chosen which will both control the pH of the composition within PHMB's effective range and provide the foaming ability necessary to physically clean the eyelid.

Advantageously, controlling the pH of the composition with a surfactant solution rather than traditional pH adjusters has safety benefits as many traditional pH adjusters are irritating to the eye. In general, surfactants are less irritating to the eye than traditional pH adjusters. Examples of traditional pH adjusters, include basic pH adjusters, such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine), and acidic pH adjusters, such as mineral acids and polycarboxylic acids (e.g., hydrochloric acid, nitric acid, phosphoric acid, sulfuric acid, citric acid, glycolic acid, and lactic acid).

In addition to reduced irritation, many surfactants have the added capability of producing a foam which assists in the cleansing ability of the composition. To form the pH stabilizing surfactant solution, one or more foam producing surfactants are first chosen to provide the foaming ability of the composition. Suitable surfactants include anionic, nonionic, and amphoteric surfactants. In one embodiment, both polyoxyethylene 80 sorbitan monolaurate and decyl polyglucoside are used as the foam producing surfactants.

To control the pH of the composition, one or more additional surfactants may be required in the pH stabilizing surfactant solution to compensate for the pH level of the foam producing surfactants. To determine whether a pH compensating surfactant is required, the pH of the foam producing surfactants is measured and a pH compensating surfactant is chosen to control the pH of the solution within the desired range. For example, if the pH level of the foam producing surfactants is in the acidic range, i.e. less that 7.0, a pH compensating surfactant in the basic range is chosen. Suitable pH compensating surfactants include both foaming and non-foaming surfactants, which further include anionic, nonionic, and amphoteric surfactants. In one embodiment, the pH compensating surfactant is cocoamphodicetate disodium.

The combination of surfactants is added to a modified Ringer's solution. For the purposes of this invention, a modified Ringer's solution is an isotonic aqueous solution of electrolytes which is physiologically compatible with human tissue. In one embodiment, the modified Ringer's solution comprises sodium chloride, potassium chloride, calcium chloride, and water. Modified Ringer's solution is included in the surfactant solution to ensure that the composition will not remove water from human tissue by osmosis.

The combination of surfactants and modified Ringer's solution are mixed with the combination of PHMB, 1,2-hexanediol, and 1,2-octanediol to form the eyelid scrub composition. To determine the correct amount of each surfactant to include in the eyelid scrub composition, the pH of the entire composition, the foaming capacity of composition, and the cleansing ability of the composition are tested. The pH level of the composition is measured with a pH meter and the amount of the individual surfactants adjusted to control the composition's pH within the desired pH range.

The composition's foaming capability is measured according to the Ross Miles method. This measurement involves producing foam from the composition and measuring the height and stability of the foam over time. The foam is created by pouring the composition from a set height into itself for five minutes. Alternatively, where the composition has a low foam capability, the composition is agitated with a turbine agitator for a set time to produce the foam. The thickness of the foam is measured at timed intervals. To achieve the desired foaming capability, the amounts of foam producing surfactants in the composition are varied.

Finally, the cleansing capabilities of the composition are tested by anecdotal human testing. Humans apply the composition to the eyelid and cleanse the eyelid. The humans report the levels of irritation, skin tightness and overall feeling of cleanness caused by the composition. The amounts and types of surfactants employed are adjusted in response to the reports.

Through the adjustment of the amounts and types of surfactants used in the pH stabilizing surfactant solution in response to test results of the pH level, foaming capacity, and cleansing capabilities, an effective amount of pH stabilizing surfactant composition to be used is determined. The combination of the pH stabilizing surfactant solution with PHMB, 1,2-hexanediol and 1,2-octanediol forms the composition of this invention.

In a first embodiment, the composition of this invention comprises PHMB, 1,2-hexanediol, and 1,2-octanediol in combination with a pH stabilizing surfactant solution. Suitable surfactants to be used in the pH stabilizing surfactant solution include amphoteric surfactants, anionic surfactants, and nonionic surfactants. Suitable amphoteric surfactants include, but are not limited to alkyldimethyl betaines, alkylamido betaines, sulfobetaines, and imidazoline amphoterics. Suitable anionic surfactants include, but are not limited to fatty alcohol sulfates, alpha olein sulfonates, sulfosuccinates, sarcosinates, phosphate esters, and carboxylates. Suitable nonionic surfactants include, but are not limited to alkanolamids, ethoxylate amids, esters, aixylated alcohols, alkylpolyglucosides, amine oxides, sorbitan esters, and ethoxylates.

In one embodiment, the pH stabilizing surfactant solution comprises cocoamphodiacetate disodium, polyoxyethylene 80 sorbitan monolaurate, decyl polyglucoside, and a modified Ringer's solution. Cocoamphodiacetate disodium is an amphoteric surfactant. Polyoxyethylene 80 sorbitan monolaurate and decyl polyglucoside are both nonionic surfactants. In another embodiment, the composition, when mixed, comprises about 0.1 to 25 wt. % cocoamphodiacetate disodium, 0.1 to 10 wt. % polyoxyethylene 80 sorbitan monolaurate, 0.2 to 10 wt. % decyl polyglucoside, and 60 to 98 wt. % modified Ringer's solution.

In another embodiment of the invention, the modified Ringer's solution comprises, sodium chloride, potassium chloride, calcium chloride, and water. Preferably, the water used is purified water. The modified Ringer's solution may also comprise 0.05 to 1.2 wt. % sodium chloride, 0.005 to 0.5 wt. % potassium chloride, 0.005 to 0.5 wt. % calcium chloride, and water. In still another embodiment, the modified Ringer's solution comprises about 0.7 wt. % sodium chloride, about 0.03 wt. % potassium chloride, about 0.033 wt. % calcium chloride, and purified water.

In still another embodiment, the composition of this invention can further comprise one or more moisturizers. Moisturizers are chemicals that prevent transepidermal water loss. Moisturizers may prevent water loss by forming a film over the skin to prevent water from evaporating from the skin. Alternatively, moisturizers comprise hydroscopic molecules that draw water from the air into the skin. Suitable moisturizers include, but are not limited to, methyl gluceth-20, sorbital, glycerine, propylene glycol, carboxylates, amino acids, glucoside derivatives, urea, lactates, and derivatives of pantothenic acid. Examples of derivatives of pantothenic acid include panthenol, D-panthenol, and D, L-panthenol.

In a further embodiment, the composition also comprises a foam stabilizer. A foam stabilizer is a chemical which increases the lifetime of the foam. The foam stabilizer can be a polyethylene glycol diester of methyl glucose and a fatty acid. Suitable fatty acids include oleic acid, steric acid, lauric acid, caprylic acid, and capric acid. Suitably, the foam stabilizer is PEG-120 methyl glucose dioleate.

One specific embodiment of the composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate. Decyl polyglucoside is sold under the tradename Oramix NS10 by Seppic, Inc. Polyoxyethylene-80 sorbitan monolaurate is sold under the tradename T-MAZ® 28 by BASF Corporation. Cocoamphodiacetate disodium is sold under the tradename Mackam 2C by The Mcintyre Group. Methyl gluceth-20 is sold under the tradename Glucam® E-20 by Dow. PEG-120 methyl glucose dioleate is sold under the tradename Glucamate DOE-120 by Dow. D-panthenol is also known as Dexpanthenol and is available from Dow.

Another specific embodiment of the composition comprises about 0.02 wt. % to about 0.3 wt. % PHMB, about 0.05 wt. % to about 2.0 wt. % 1,2-hexanediol, about 0.05 wt. % to about 2.0 wt. % 1,2-octanediol, about 0.1 wt. % to about 25 wt. % cocoamphodiacetate disodium, about 0.1 wt. % to about 10 wt. % polyoxyethylene 80 sorbitan monolaurate, about 0.2 wt. % to about 10 wt. % decyl polyglucoside, and about 60 wt. % to about 98 wt. % Modified Ringer's Solution.

Yet another specific embodiment of the composition comprises about 0.04 wt. % polyhexamethylene biguanide, about 0.2 wt. % 1,2-hexanediol, about 0.2 wt. % 1,2-octanediol, about 0.2 wt. % D-panthenol, about 0.215 wt. % cocoamphodiacetate disodium, about 4.032 wt. % polyoxyethylene 80 sorbitan monolaurate, about 0.275 wt. % decyl polyglucoside, about 4.3 wt. % methyl gluceth-20, about 0.6 wt. % PEG-120 methyl glucose dioleate, about 87.985 wt. % Modified Ringer's Solution, and water.

Zinc Free

Zinc salts are astringents which cause skin to tighten. The skin around the ocular area is more sensitive that other areas of skin. The inclusion of a zinc salt is a composition may be undesirable as its astringent property would make the composition more irritating to the eyelid area. Therefore in one embodiment, the composition comprises PHMB, 1,2-hexanediol, 1,2-octanediol, and a pH stabilizing surfactant solution, but is also essentially free of zinc salts. Examples of zinc salts include zinc acetate, zinc lactate, zinc gluconate, zinc citrate, zinc butyrate, and zinc sterate.

Methods

To produce the composition of this invention, the modified Ringer's solution is made by mixing electrolytes in water. Symdiol, a combination of 1,2-hexanediol and 1,2-octanediol, is mixed with the modified Ringer's solution along with the surfactants that comprise the pH stabilizing surfactant solution. The mixture is then heated to dissolve the solids into solution. The mixture is then allowed to cool before the polyhexamethylene biguanide is added. In one aspect of the method, the mixture is heated to about 60° C. In another aspect, the mixture is allowed to cool until its temperature reaches about 40° C.

In another embodiment of the method of producing the composition, the modified Ringer's solution is made by mixing sodium chloride, potassium chloride, and calcium chloride with water. In still another embodiment, one or more moisturizers are also added to the modified Ringer's solution. A foam stabilizer may also be included.

The composition of the present invention may be used to cleanse an eyelid. The eyelid scrub is useful in preoperative sterilization of the eyelid and in everyday application for the prevention of various diseases of the eyelid, such as blepharitis. To cleanse the eyelid, an effective amount of the eyelid scrub is applied to the eyelid. The eyelid scrub comprises polyhexamethylene biguanide, 1,2-hexanediol, 1,2-octanediol, and a pH stabilizing surfactant solution present in an amount effective to control the pH level of the composition between 5.5 and 7.5. The eyelid scrub may be rubbed on the eyelid scrub to induce foaming, which facilitates cleansing of the eyelid. Advantageously, the eyelid scrub of this invention can be mild enough that it can be allowed to remain on the eyelid after cleansing, without rinsing. The ability of the eyelid scrub to be left on the eyelid rather than rinsed off increases the composition's anti-microbial effect. In general, the longer an anti-microbial composition is allowed to contact the pathogens, the more pathogens it will kill.

In another aspect of the method of using the composition of this invention, the eyelid scrub is applied to the eyelid from a fabric pad. The eyelid scrub may be rubbed on the eyelid with a fabric pad to induce foaming, which assists in the cleansing ability of the eyelid scrub.

Pre-Moistened Pads

Referring now to FIG. 1, the composition of the present invention may be combined with a fabric pad 1 to form an apparatus for cleansing eyelids. In a first embodiment, the apparatus comprises a fabric pad 1 pre-moistened with an eyelid scrub composition. The eyelid scrub composition comprising polyhexamethylene biguanide, 1,2-hexanediol, 1,2-octanediol, and a pH stabilizing surfactant solution present in an amount effective to control the pH level of the composition between 5.5 and 7.5. In one aspect, the fabric pad 1 comprises a rayon and polypropylene fabric blend. In another aspect, the fabric pad comprises a textured surface 2.

Figure 2:
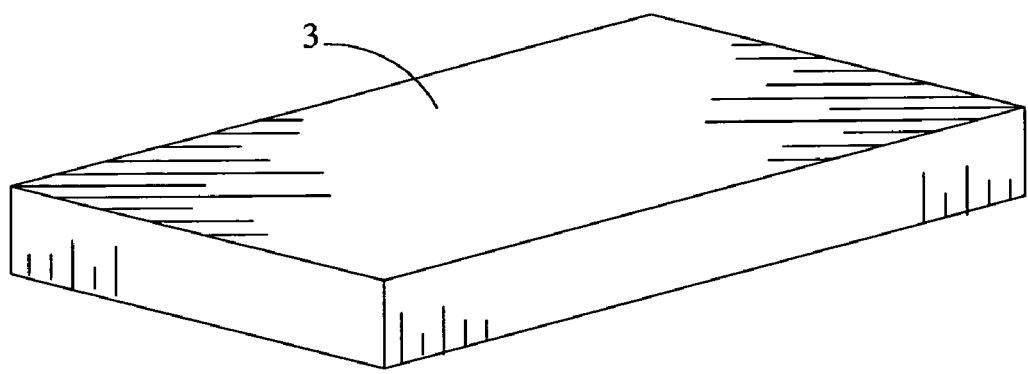
FIG. 2 is a top view of the container for the fabric pad.

Referring now to FIG. 2, in another embodiment, the apparatus further comprises a sealable container 3 enclosing the pre-moistened fabric pad. In one aspect, the sealable container 3 may comprise a box, or a package. The package may be made of any suitable material including plastic or a metal foil material. The pre-moistened fabric pads may be individually packaged for use. In still another embodiment, the apparatus comprises 1.3 to 1.5 grams of eyelid scrub. Preferably, the 1.4 grams of eyelid scrub are used.

Test Results

The composition of the present invention has an anti-microbial effect with a lower level on irritation than other anti-microbial compositions. To confirm the characteristic of the composition of this invention both the irritation and antimicrobial effects of the composition were tested. These results were compared to another commonly available composition, Sterelid®.

One embodiment of the composition of this invention was tested for both irritation and anti-microbial effect, hereafter referred to as Composition 1. Composition 1 contained polyhexamethylene biguanide, 1,2-hexanediol, 1,2-octanediol, D-panthenol, cocoamphodiacetate disodium, polyoxyethylene 80 sorbitan monolaurate, decyl polyglucoside, methyl gluceth-20, PEG-120 methyl glucose dioleate, Modified Ringer's Solution, and water.

For comparison a commonly available eyelid scrub was also tested. Sterilid®, available from Advanced Vision, contains water, PEG-80, sorbitan laurate, sodium trideceth sulfate, cocamidopropyl betaine, sodium lauroamphacetate, PEG-150 distearate, sodium laureth-13 carboxylate, linalool oil, hepes acetate, sodium perborate monohydrate, panthenol, allantoin, sodium chloride, tea tree oil, Tris-EDTA, boric acid, cocamidopropyl PG-dimonium chloride, etidronic acid, phosphonic acid, with citric acid and sodium hydroxide for pH adjustment.

To determine the irritation level of the composition, an eye irritation study was performed and the results scored on the Draize Scale for Scoring Ocular Lesions. The irritation testing was performed by placing 0.1 ml of the composition in the conjunctival sac of a rabbit's eye and recording the size and intensity of ocular irritation at 1, 24, 48, and 72 hours. The information is translated into a score on the Draize Scale which represents the irritation caused by the composition.

The results of the irritation testing for both Composition 1 and Sterilid are presented in Table 1. Composition 1 scored and 1.67 out of a possible 110.0 on the Draize Scale. A 1.67 is classified as "Practically Non-irritating" on the Draize Scale. Sterilid scored a 4.0 on the Draize Scale, which is classified as "Minimally Irritating."

TABLE 1

Eye Irritation Testing/Draize Score

| Composition | Mean Irritation Score |
|---|---|
| Composition 1 | 1.67/110.0 |
| Sterilid | 4.0/110.0 |

Both Composition 1 and Sterilid were also subjected to time-kill studies to determine their effectiveness against the pathogen *Staphylococcus Epidermidis* (*S. Epidermidis*), which is a leading cause of post-operative endophthalmitis, a type of post-operative infection. The time-kill testing involved subjecting a suspension of the pathogen to the composition for 60 seconds and then neutralizing the composition. The pathogen was then plated and incubated for the appropriate amount of time. After incubation, the number of colonies of the pathogen were counted and the logarithmic reduction (Log Reduction) of the colony count from the control's colony count was calculated. The results of the time-kill study are presented in Table 2.

TABLE 2

Time-Kill Testing of *S. Epidermidis*

| Composition | Log Reduction |
|---|---|
| Composition 1 | 5.5 |
| Sterilid | 3.5 |

Composition 1 was found to have a Log reduction of 5.5 of *S. Epidermidis*, while Sterilid was found to have Log reduction of 3.5 of *S. Epidermidis*. Composition 1's ability to kill the *S. Epidermidis* pathogen was therefore greater that Sterilid's.

The results of the irritation and time-kill testing indicate that Composition 1 was both more effective and less irritating than Sterilid, which uses citric acid and sodium hydroxide for pH adjustment rather than the pH modifying surfactant solution of the present invention.

While the invention has been described with reference to several embodiments, it will be understood by those skilled in the art that various changes in form and detail may be made therein without departing from the spirit and scope of the invention. Also, the composition is described as useful as an eyelid cleanser. It should be readily understood that the composition of this invention may be used for other applications.

The invention claimed is:

1. An eyelid scrub composition comprising:
polyhexamethylene biguanide;
1,2-hexanediol;
1,2-octanediol;
about 60 wt. % to about 98 wt. % modified Ringer's solution: and a surfactant solution comprising: one or more amphoteric surfactants present in an amount effective to control a pH of the composition to within a desired pH range, the one or more amphoteric surfactants comprising: one or more pH compensating surfactants comprising about 0.1 wt. % to about 25 wt. % cocoamphodiacetate disodium, the surfactant solution further comprising: a mixture of one or more foam-producing surfactants comprising at least one of: about 0.1 wt. % to about 10 wt. % polyoxyethylene-80 sorbitan monolaurate: and about 0.2 wt. % to about 10 wt. % decyl polyglucoside, wherein an amount and a type of each of the pH compensating surfactants is determined based on a measured pH of the mixture of foam-producing surfactants.

2. The eyelid scrub composition of claim 1, the one or more amphoteric surfactants being selected from a group consisting of: alkyldimethyl betaines, alkylamido betaines, sulfobetaines, and imidazoline amphoterics.

3. The eyelid scrub composition of claim 1, the one or more pH compensating surfactants being added to the mixture of foam-producing surfactants in an amount effective to maintain the pH of the composition between about 5.5 and about 7.5.

4. The eyelid scrub composition of claim 1, the modified Ringer's solution comprising:
sodium chloride;
potassium chloride;
calcium chloride; and water.

5. The eyelid scrub composition of claim 4, the modified Ringer's solution comprising:
0.05 to 1.2 wt. % sodium chloride;
0.005 to 0.5 wt. % potassium chloride;
0.005 to 0.5 wt. % calcium chloride; and water.

6. The eyelid scrub composition of claim 4, the modified Ringer's solution comprising:
0.7 wt. % sodium chloride;
0.03 wt. % potassium chloride;
0.033 wt. % calcium chloride; and purified water.

7. The eyelid scrub composition of claim 1, the composition further comprising:
one or more moisturizers selected from a group consisting of: methyl gluceth-20, sorbitol, glycerin, glycols, propylene glycol, carboxylates, amino acids, glucosides, urea, lactates, panthenol, D-panthenol, D, L-panthenol, and combinations thereof.

8. The eyelid scrub composition of claim 7, the composition further comprising: one or more foam stabilizers.

9. The eyelid scrub composition of claim 8, the one or more foam stabilizers comprising a polyethylene glycol diester of methyl glucose and a fatty acid.

10. The eyelid scrub composition of claim 9, the fatty acid being selected from a group consisting of oleic acid, steric acid, lauric acid, caprylic acid, and capric acid.

11. The eyelid scrub composition of claim 10, the one or more foam stabilizers comprising PEG-120 methyl glucose dioleate.

12. A method for forming the eyelid scrub composition of claim 1, the method comprising: preparing the modified Ringer's solution by mixing one or more electrolytes in water; mixing 1,2-hexanediol, 1,2-octanediol, and an effective amount of the surfactant solution with the modified Ringer's solution to form a mixture; heating the mixture; allowing the mixture to cool; and adding polyhexamethylene biguanide to the cooled mixture, wherein, the surfactant solution is formed by: mixing together the one or more foam-producing surfactants comprising polyethylene-80 sorbitan monolaurate and decyl polyglucoside, measuring a pH of the one or more foam-producing surfactants, and mixing the one or more amphoteric surfactants cocoamphodiactate disodium as pH compensating surfactants with the one or more foam-producing surfactants in dependence on the measured pH of the foam-producing surfactants to generate the surfactant solution.

13. The method of claim 12, wherein: on the condition that the measured pH of the one or more foam-producing surfactants is in a basic pH range, the one or more amphoteric surfactants added to the foam-producing surfactants comprise at least one amphoteric surfactant having a primarily acidic characteristic when present in the basic pH range, and on the condition that the measured pH of the one or more foam-producing surfactants is in an acidic pH range, the one or more amphoteric surfactants added to the foam-producing surfactants comprise at least one amphoteric surfactant having a primarily basic characteristic when present in the acidic pH range.

14. The method of claim 12, the step of preparing the modified Ringer's solution comprising: mixing sodium chloride, potassium chloride, and calcium chloride with water.

15. The method of claim 12, further comprising: mixing one or more moisturizers with the modified Ringer's solution.

16. The method of claim 15, further comprising: mixing one or more foam stabilizers with the modified Ringer's solution.

17. The method of claim 12, wherein the mixture is heated to about 60° C.

18. The method of claim 12, further comprising: allowing one or more solids present in the mixture to dissolve prior to cooling the mixture.

19. The method of claim 12, wherein the mixture is cooled to about 40° C.

20. An eyelid scrub composition comprising:
about 0.02 wt. % to about 0.3 wt. % polyhexamethylene biguanide;
about 0.05 wt. % to about 2.0 wt. % 1, 2-hexanediol;
about 0.05 wt. % to about 2.0 wt. % 1, 2-octanediol;
about 60 wt. % to about 98 wt. % modified Ringer's solution;
one or more foam-producing surfactants comprising:
about 0.1 wt. % to about 10 wt. % polyoxyethylene-80 sorbitan
monolaurate: and about 0.2 wt. % to about 10 wt. % decyl polyglucoside;
one or more pH compensating surfactants present in an amount effective
to maintain a pH of the composition within a desired range, the pH
compensating surfactants comprising;
about 0.1 wt. % to about 25 wt. % cocoamphodiacetate disodium; one or
more moisturizers comprising; methyl gluceth-20; and D-panthenol; and
one or more foam stabilizers comprising; PEG-120 methyl glucose dioleate.

21. The eyelid scrub composition of claim 20, the composition further comprising:
about 0.05 wt. % to about 5.0 wt. % D-panthenol;
about 1.0 wt. % to about 20 wt. % methyl gluceth-20; and
about 0.1 wt. % to about 5 wt. % PEG-120 methyl glucose dioleate.

22. The eyelid scrub composition of claim 20, the composition comprising:
about 0.04 wt. % polyhexamethylene biguanide;
about 0.2 wt. % 1, 2-hexancdiol:
about 0.2 wt. % 1, 2-octanediol;
about 0.2 wt. % D-panthenol;
about 0.215 wt. % cocoamphodiacetate disodium;
about 4.032 wt. % polyoxyethylene-80 sorbitan monolaurate;
about 0.275 wt. % decyl polyglucoside;
about 4.3 wt. % methyl gluceth-20;
about 0.6 wt. % PEG-120 methyl glucose dioleate: and
about 87.985 wt. % Modified Ringer's solution; the composition further
comprising: about 1.953 wt % water.

* * * * *